US006239266B1

(12) United States Patent
Pribill et al.

(10) Patent No.: US 6,239,266 B1
(45) Date of Patent: May 29, 2001

(54) ZAP-3 TUMOR ASSOCIATED GENES AND THEIR USES

(76) Inventors: Ingrid Pribill, Pfeilgasse 51/7, Vienna (AT), A-1080; David Munroe, 2203 Montgomery Ave., Cardiff, CA (US) 92007

( * ) Notice: Subject to any disclaimer, the term of this patent is extended or adjusted under 35 U.S.C. 154(b) by 0 days.

(21) Appl. No.: 09/347,488

(22) Filed: Jul. 2, 1999

Related U.S. Application Data
(60) Provisional application No. 60/091,980, filed on Jul. 7, 1998, and provisional application No. 60/092,414, filed on Jul. 10, 1998.

(51) Int. Cl.[7] .............................. C07H 5/04; C07H 5/06; C07H 19/00; C07H 21/00; C07H 21/02
(52) U.S. Cl. ........................... 536/23.2; 536/1; 536/18.7; 536/22.1; 536/23.1
(58) Field of Search ................................. 536/23.1, 22.1, 536/18.7, 1, 23.2

(56) References Cited

PUBLICATIONS

Zhao, Hong G. et al. The molecular basis of Sanfilippo syndrome type B. Proc. Natl. Acad. Sci. USA, 93:6101–6105, 1996.*
Amino Acid database, Accession #U43572, 1996.*
Bennett et al., "cDNA Cloning and Expression of a Novel Human UDP–N–acetyl–α–D–galactosamine," (Jul. 19, 1996) *J. Biol. Chem.* vol. 271(29):17006–17012.
Buchhagen et al., "Two Regions of Homozygosity on Chromosome 3p in Squamous Cell Carcinoma of the Head and Neck: Comparison with Cytogenetic Analysis" (Nov./Dec. 1996) *Head & Neck* vol. 18(6):529–537.
Dahiya et al., "Chromosomes 3p24–26 and 3p22–12 Loss in Human Prostatic Adenocarcinoma" (1997) *Int J Cancer* vol. 71(1):20–25.
Hanski et al., "Alteration of Mucin–bound Carbohydrate Moieties in Malignant Transformation of Colonic Mucosa," (Nov./Dec. 1992) *Cancer Journal* vol. 5 (6):332–342.
Kleene et al., "The Molecular and Cell Biology of Glycosyltransferases," (1993) *Biochim Biophys Act.* vol. 1154:283–325.

Li et al, "Chromosome 3 Allelic Losses and Microsatellite Alterations in Transitional Cell Carcinoma of the Urinary Bladder," (Jul. 1, 1996) *Am J Pathol* vol. 149(1):229–235.
Matsumoto et al., "Detailed Deletion Mapping of Chromosome Arm 3p in Breast Cancers: A2–cM Region on 3p14.3–21.1 and 5–cM Region on 3p24.2–25.1 Commonly Deleted in Tumors," (1997) *Genes Chromsomes Cancer* vol. 20:268–274.
Meurer et al., "cDNA Cloning, Expression and Chromosomal Localization of a Human UDP–GalNAc:Polypeptide, N–Acetylgalactosaminyltransferase," (1995) *J. Biochem.* vol. 118:568–574.
Sikkink et al., "Deletion Mapping of Chromosomes 3p and 13q and Preliminary Analysis of the FHIT Gene in Human Nonmelanoma Skin Cancer" (Aug. 9, 1997) *J Invest Dermatol* vol. 109(6):801–805.
White et al. "Purification and cDNA Cloning of a Human UDP–N–acetyl–α–D–galactosamine:polypeptide N–Acetylgalactosaminyltransferase," (Oct. 13, 1995) *J. Biol. Chem.* vol. 270(41):24156–24165.
Genbank Accession No. AA971319, Sep. 24, 1998.
Genbank Accession No. AA236602, Aug. 7, 1997.
Genbank Accession No. AA055179, Sep. 17, 1996.
Genbank Accession No. AA055174, Sep. 17, 1996.
Genbank Accession No. AA055297, Sep. 17, 1996.
Genbank Accession No. AA368180, Apr. 21, 1997.
Genbank Accession No. W12343, Oct. 02, 1997.

* cited by examiner

*Primary Examiner*—Anthony C. Caruta
*Assistant Examiner*—Alama M. Harris
(74) *Attorney, Agent, or Firm*—Pamela J. Sherwood; Bozicevic, Field & Francis LLP

(57) ABSTRACT

Methods for isolating ZAP-3 genes are provided. Deletion of the ZAP-3 locus is associated with human tumors, particularly carcinomas. The ZAP-3 nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as treatment of cancer, identification of cell type based on expression, and the like.

12 Claims, No Drawings

SEQUENCE LISTING

<160> NUMBER OF SEQ ID NOS: 2

<210> SEQ ID NO 1
<211> LENGTH: 3332
<212> TYPE: DNA
<213> ORGANISM: H. sapiens
<220> FEATURE:
<221> NAME/KEY: CDS
<222> LOCATION: (368)...(2284)

<400> SEQUENCE: 1

```
tttatacaaa gggggaaaga aacacctgag cagaatggaa tcattatttt tttcccaagg      60
agaaaaccgg ggtaaaggga gggaagcaat tcaatttgaa gtccctgtga atgggctttc     120
agaaggcaat taaagaaatc cactcagaga ggacttgggg tgaaacttgg gtcctgtggt     180
tttctgattg taagtggaag caggtcttgc acacgctgtt ggcaaatgtc aggaccaggt     240
taagtgactg gcagaaaaac ttccaggtgg aacaagcaac ccaggttctg ctgcaagctt     300
gaaggagcct ggagcgggag aaagctaact tgaacatgac ctgttgcatt tggcaagttc     360 tagcaac atg ctc cta agg aag cga tac agg cac aga cca tgc aga ctc      409
        Met Leu Leu Arg Lys Arg Tyr Arg His Arg Pro Cys Arg Leu
         1               5                  10
```

```
cag ttc ctc ctg ctg ctc ctg atg ctg gga tgc gtc ctg atg atg gtg      457
Gln Phe Leu Leu Leu Leu Leu Met Leu Gly Cys Val Leu Met Met Val
 15                  20                  25                  30 gcg atg ttg cac cct ccc cac cac acc ctg cac cag act gtc aca gcc      505
Ala Met Leu His Pro Pro His His Thr Leu His Gln Thr Val Thr Ala
                 35                  40                  45 caa gcc agc aag cac agc cct gaa gcc agg tac cgc ctg gac ttt ggg      553
Gln Ala Ser Lys His Ser Pro Glu Ala Arg Tyr Arg Leu Asp Phe Gly
             50                  55                  60 gaa tcc cag gat tgg gta ctg gaa gct gag gat gag ggt gaa gag tac      601
Glu Ser Gln Asp Trp Val Leu Glu Ala Glu Asp Glu Gly Glu Glu Tyr
         65                  70                  75 agc cct ctg gag ggc ctg cca ccc ttt atc tca ctg cgg gag gat cag      649
Ser Pro Leu Glu Gly Leu Pro Pro Phe Ile Ser Leu Arg Glu Asp Gln
     80                  85                  90 ctg ctg gtg gcc gtg gcc tta ccc cag gcc aga agg aac cag agc cag      697
Leu Leu Val Ala Val Ala Leu Pro Gln Ala Arg Arg Asn Gln Ser Gln
 95                 100                 105                 110 ggc agg aga ggt ggg agc tac cgc ctc atc aag cag cca agg agg cag      745
Gly Arg Arg Gly Gly Ser Tyr Arg Leu Ile Lys Gln Pro Arg Arg Gln
                115                 120                 125 gat aag gaa gcc cca aag agg gac tgg ggg gct gat gag gac ggg gag      793
Asp Lys Glu Ala Pro Lys Arg Asp Trp Gly Ala Asp Glu Asp Gly Glu
            130                 135                 140 gtg tct gaa gaa gag gag ttg acc ccg ttc agc ctg gac cca cgt ggc      841
Val Ser Glu Glu Glu Glu Leu Thr Pro Phe Ser Leu Asp Pro Arg Gly
        145                 150                 155 ctc cag gag gca ctc agt gcc cgc atc ccc ctc cag agg gct ctg ccc      889
Leu Gln Glu Ala Leu Ser Ala Arg Ile Pro Leu Gln Arg Ala Leu Pro
    160                 165                 170 gag gtg cgg cac cca ctg tgt ctg cag cag cac cct cag gac agc ctg      937
Glu Val Arg His Pro Leu Cys Leu Gln Gln His Pro Gln Asp Ser Leu
175                 180                 185                 190 ccc aca gcc agc gtc atc ctc tgt ttc cat gat gag gcc tgg tcc act      985
Pro Thr Ala Ser Val Ile Leu Cys Phe His Asp Glu Ala Trp Ser Thr
                195                 200                 205 ctc ctg cgg act gta cac agc atc ctc gac aca gtg ccc agg gcc ttc     1033
Leu Leu Arg Thr Val His Ser Ile Leu Asp Thr Val Pro Arg Ala Phe
            210                 215                 220 ctg aag gag atc atc ctc gtg gac gac ctc agc cag caa gga caa ctc     1081
Leu Lys Glu Ile Ile Leu Val Asp Asp Leu Ser Gln Gln Gly Gln Leu
        225                 230                 235 aag tct gct ctc agc gaa tat gtg gcc agg ctg gag ggg gtg aag tta     1129
Lys Ser Ala Leu Ser Glu Tyr Val Ala Arg Leu Glu Gly Val Lys Leu
    240                 245                 250 ctc agg agc aac aag agg ctg agt gcc atc agg gcc cgg atg ctg ggg     1177
Leu Arg Ser Asn Lys Arg Leu Ser Ala Ile Arg Ala Arg Met Leu Gly
255                 260                 265                 270 gcc acc aga gcc acc ggg gat gtg ctc gtc ttc atg gat gcc cac tgc     1225
Ala Thr Arg Ala Thr Gly Asp Val Leu Val Phe Met Asp Ala His Cys
                275                 280                 285 gag tgc cac cca ggc tgg ctg gag ccc ctc ctc agc aga ata gct ggt     1273
Glu Cys His Pro Gly Trp Leu Glu Pro Leu Leu Ser Arg Ile Ala Gly
            290                 295                 300 gac agg agc cga gtg gta tct ccg gtg ata gat gtg att gac tgg aag     1321
Asp Arg Ser Arg Val Val Ser Pro Val Ile Asp Val Ile Asp Trp Lys
        305                 310                 315 act ttc cag tat tac ccc tca aag gac ctg cag cgt ggg gtg ttg gac     1369
Thr Phe Gln Tyr Tyr Pro Ser Lys Asp Leu Gln Arg Gly Val Leu Asp
```

-continued

```
            320                 325                 330
tgg aag ctg gat ttc cac tgg gaa cct ttg cca gag cat gtg agg aag    1417
Trp Lys Leu Asp Phe His Trp Glu Pro Leu Pro Glu His Val Arg Lys
335                 340                 345                 350 gcc ctc cag tcc ccc ata agc ccc atc agg agc cct gtg gtg ccc gga    1465
Ala Leu Gln Ser Pro Ile Ser Pro Ile Arg Ser Pro Val Val Pro Gly
                    355                 360                 365 gag gtg gtg gcc atg gac aga cat tac ttc caa aac act gga gcg tat    1513
Glu Val Val Ala Met Asp Arg His Tyr Phe Gln Asn Thr Gly Ala Tyr
                370                 375                 380 gac tct ctt atg tcg ctg cga ggt ggt gaa aac ctc gaa ctg tct ttc    1561
Asp Ser Leu Met Ser Leu Arg Gly Gly Glu Asn Leu Glu Leu Ser Phe
            385                 390                 395 aag gcc tgg ctc tgt ggt ggc tct gtt gaa atc ctt ccc tgc tct cgg    1609
Lys Ala Trp Leu Cys Gly Gly Ser Val Glu Ile Leu Pro Cys Ser Arg
        400                 405                 410 gta gga cac atc tac caa aat cag gat tcc cat tcc ccc ctc gac cag    1657
Val Gly His Ile Tyr Gln Asn Gln Asp Ser His Ser Pro Leu Asp Gln
415                 420                 425                 430 gag gcc acc ctg agg aac agg gtt cgc att gct gag acc tgg ctg ggg    1705
Glu Ala Thr Leu Arg Asn Arg Val Arg Ile Ala Glu Thr Trp Leu Gly
                    435                 440                 445 tca ttc aaa gaa acc ttc tac aag cat agc cca gag gcc ttc tcc ttg    1753
Ser Phe Lys Glu Thr Phe Tyr Lys His Ser Pro Glu Ala Phe Ser Leu
                450                 455                 460 agc aag gct gag aag cca gac tgc atg gaa cgc ttg cag ctg caa agg    1801
Ser Lys Ala Glu Lys Pro Asp Cys Met Glu Arg Leu Gln Leu Gln Arg
            465                 470                 475 aga ctg ggt tgt cgg aca ttc cac tgg ttt ctg gct aat gtc tac cct    1849
Arg Leu Gly Cys Arg Thr Phe His Trp Phe Leu Ala Asn Val Tyr Pro
480                 485                 490 gag ctg tac cca tct gaa ccc agg ccc agt ttc tct gga aag ctc cac    1897
Glu Leu Tyr Pro Ser Glu Pro Arg Pro Ser Phe Ser Gly Lys Leu His
495                 500                 505                 510 aac act gga ctt ggg ctc tgt gca gac tgc cag gca gaa ggg gac atc    1945
Asn Thr Gly Leu Gly Leu Cys Ala Asp Cys Gln Ala Glu Gly Asp Ile
                    515                 520                 525 ctg ggc tgt ccc atg gtg ttg gct cct tgc agt gac agc cgg cag caa    1993
Leu Gly Cys Pro Met Val Leu Ala Pro Cys Ser Asp Ser Arg Gln Gln
                530                 535                 540 cag tac ctg cag cac acc agc agg aag gag att cac ttt ggc agc cca    2041
Gln Tyr Leu Gln His Thr Ser Arg Lys Glu Ile His Phe Gly Ser Pro
            545                 550                 555 cag cac ctg tgc ttt gct gtc agg cag gag cag gtg att ctt cag aac    2089
Gln His Leu Cys Phe Ala Val Arg Gln Glu Gln Val Ile Leu Gln Asn
        560                 565                 570 tgc acg gag gaa ggc ctg gcc atc cac cag cag cac tgg gac ttc cag    2137
Cys Thr Glu Glu Gly Leu Ala Ile His Gln Gln His Trp Asp Phe Gln
575                 580                 585                 590 gag aat ggg atg att gtc cac att ctt tct ggg aaa tgc atg gaa gct    2185
Glu Asn Gly Met Ile Val His Ile Leu Ser Gly Lys Cys Met Glu Ala
                    595                 600                 605 gtg gtg caa gaa aac aat aaa gat ttg tac ctg cgt ccg tgt gat gga    2233
Val Val Gln Glu Asn Asn Lys Asp Leu Tyr Leu Arg Pro Cys Asp Gly
                610                 615                 620 aaa gcc cgc cag cag tgg cgt ttt gac cag atc aat gct gtg gat gaa    2281
Lys Ala Arg Gln Gln Trp Arg Phe Asp Gln Ile Asn Ala Val Asp Glu
            625                 630                 635 cga tgaatgtcaa tgtcagaagg aaaagagaat tttggccatc aaaatccagc         2334
Arg
```

-continued

```
tccaagtgaa cttaaagagc ttatatattt catgaagctg atccttttgt gtgtgtgctc    2394
ctggtgttag gagagaaaaa agctctatga aagaatatag gaagtttctc cttttcacac    2454
cttatttcat tgactgctgg ctgctttaaa aaaaaaaaaa aggatccatt gtaccgttgt    2514
cttcatcact gggaaatgat tattacatag tacagaagat tctttgtttt tctccactga    2574
gcacttaaca attgctttct ctctggcctg gacattctct ggcagcacct ccaggataca    2634
taaattcaat ggatcaattt atttgtcttc aaatggcctt aacttggatt gtctgtttgg    2694
ccaaccatga aaattaaaga gtgaagcaga tgtaatggcc tgacattcca aaaactctga    2754
attgggttta ttagcacaaa tgttgtgttc atttgttgag ccatatctca gaagaaggaa    2814
agggagctac agaaaggagg tttaggattg cagagaagat gcaagagcac tttggcccaa    2874
ttctccagct caacccagca gctgaaaagc ttcaagagat ctaggaaaag acattttcat    2934
gttaatgaga atttccacca ttgtagagaa tttccttcct actgagaatc tacctctatt    2994 cccctgccc tagctcttct ctaacttggt taaccataac cataaccaga ttcccttgca    3054
atcgatttct ctttagtcgt tggtgttaga agtaccagca caatttgagc attcccatta    3114
acaaaggtgt tcacagttga gaaactctcc tgccgggcgc ggtggctcat gcctgtaatt    3174 ccagcactt gggaggcaga gttgggagga tcacctgatg tcaggggttt gagaccagcc    3234
tggtcaacat tgcaaaacct tgtctctact aaaaatacaa aaattagctg ggcatggtgg    3294
cgcatacctg taatcccagc tacttgggag gctgaggg                           3332
```

<210> SEQ ID NO 2
<211> LENGTH: 638
<212> TYPE: PRT
<213> ORGANISM: H. sapiens

<400> SEQUENCE: 2

```
Met Leu Leu Arg Lys Arg Tyr Arg His Arg Pro Cys Arg Leu Gln Phe
  1               5                  10                  15

Leu Leu Leu Leu Leu Met Leu Gly Cys Val Leu Met Met Val Ala Met
             20                  25                  30

Leu His Pro Pro His His Thr Leu His Gln Thr Val Thr Ala Gln Ala
         35                  40                  45

Ser Lys His Ser Pro Glu Ala Arg Tyr Arg Leu Asp Phe Gly Glu Ser
     50                  55                  60

Gln Asp Trp Val Leu Glu Ala Glu Asp Glu Gly Glu Tyr Ser Pro
 65                  70                  75                  80

Leu Glu Gly Leu Pro Pro Phe Ile Ser Leu Arg Glu Asp Gln Leu Leu
                 85                  90                  95

Val Ala Val Ala Leu Pro Gln Ala Arg Arg Asn Gln Ser Gln Gly Arg
            100                 105                 110

Arg Gly Gly Ser Tyr Arg Leu Ile Lys Gln Pro Arg Arg Gln Asp Lys
        115                 120                 125

Glu Ala Pro Lys Arg Asp Trp Gly Ala Asp Glu Asp Gly Glu Val Ser
    130                 135                 140

Glu Glu Glu Glu Leu Thr Pro Phe Ser Leu Asp Pro Arg Gly Leu Gln
145                 150                 155                 160

Glu Ala Leu Ser Ala Arg Ile Pro Leu Gln Arg Ala Leu Pro Glu Val
                165                 170                 175

Arg His Pro Leu Cys Leu Gln Gln His Pro Gln Asp Ser Leu Pro Thr
            180                 185                 190
```

-continued

```
Ala Ser Val Ile Leu Cys Phe His Asp Glu Ala Trp Ser Thr Leu Leu
            195                 200                 205

Arg Thr Val His Ser Ile Leu Asp Thr Val Pro Arg Ala Phe Leu Lys
    210                 215                 220

Glu Ile Ile Leu Val Asp Asp Leu Ser Gln Gln Gly Gln Leu Lys Ser
225                 230                 235                 240

Ala Leu Ser Glu Tyr Val Ala Arg Leu Glu Gly Val Lys Leu Leu Arg
            245                 250                 255

Ser Asn Lys Arg Leu Ser Ala Ile Arg Ala Arg Met Leu Gly Ala Thr
            260                 265                 270

Arg Ala Thr Gly Asp Val Leu Val Phe Met Asp Ala His Cys Glu Cys
            275                 280                 285

His Pro Gly Trp Leu Glu Pro Leu Leu Ser Arg Ile Ala Gly Asp Arg
    290                 295                 300

Ser Arg Val Val Ser Pro Val Ile Asp Val Ile Asp Trp Lys Thr Phe
305                 310                 315                 320

Gln Tyr Tyr Pro Ser Lys Asp Leu Gln Arg Gly Val Leu Asp Trp Lys
            325                 330                 335

Leu Asp Phe His Trp Glu Pro Leu Pro Glu His Val Arg Lys Ala Leu
            340                 345                 350

Gln Ser Pro Ile Ser Pro Ile Arg Ser Pro Val Val Pro Gly Glu Val
            355                 360                 365

Val Ala Met Asp Arg His Tyr Phe Gln Asn Thr Gly Ala Tyr Asp Ser
370                 375                 380

Leu Met Ser Leu Arg Gly Gly Glu Asn Leu Glu Leu Ser Phe Lys Ala
385                 390                 395                 400

Trp Leu Cys Gly Gly Ser Val Glu Ile Leu Pro Cys Ser Arg Val Gly
            405                 410                 415

His Ile Tyr Gln Asn Gln Asp Ser His Ser Pro Leu Asp Gln Glu Ala
            420                 425                 430

Thr Leu Arg Asn Arg Val Arg Ile Ala Glu Thr Trp Leu Gly Ser Phe
            435                 440                 445

Lys Glu Thr Phe Tyr Lys His Ser Pro Glu Ala Phe Ser Leu Ser Lys
    450                 455                 460

Ala Glu Lys Pro Asp Cys Met Glu Arg Leu Gln Leu Gln Arg Arg Leu
465                 470                 475                 480

Gly Cys Arg Thr Phe His Trp Phe Leu Ala Asn Val Tyr Pro Glu Leu
            485                 490                 495

Tyr Pro Ser Glu Pro Arg Pro Ser Phe Ser Gly Lys Leu His Asn Thr
            500                 505                 510

Gly Leu Gly Leu Cys Ala Asp Cys Gln Ala Glu Gly Asp Ile Leu Gly
            515                 520                 525

Cys Pro Met Val Leu Ala Pro Cys Ser Asp Ser Arg Gln Gln Gln Tyr
    530                 535                 540

Leu Gln His Thr Ser Arg Lys Glu Ile His Phe Gly Ser Pro Gln His
545                 550                 555                 560

Leu Cys Phe Ala Val Arg Gln Glu Gln Val Ile Leu Gln Asn Cys Thr
            565                 570                 575

Glu Glu Gly Leu Ala Ile His Gln Gln His Trp Asp Phe Gln Glu Asn
            580                 585                 590

Gly Met Ile Val His Ile Leu Ser Gly Lys Cys Met Glu Ala Val Val
            595                 600                 605
```

-continued

```
Gln Glu Asn Asn Lys Asp Leu Tyr Leu Arg Pro Cys Asp Gly Lys Ala
    610             615                 620

Arg Gln Gln Trp Arg Phe Asp Gln Ile Asn Ala Val Asp Glu
625             630             635
```

ZAP-3 TUMOR ASSOCIATED GENES AND THEIR USES

This Application claims benefit to provisional application 60/091,980 Jul. 7, 1998 which claims benefit to provisional application 60/092,414 Jul. 10, 1998.

INTRODUCTION

BACKGROUND

Control of cellular proliferation is of great importance for many normal and abnormal biological processes; including development, wound healing, programmed cell death, angiogenesis and tumorigenesis. A myriad of components involved in the regulation of cell proliferation have been identified, including growth factors, cell cycle regulators, oncogenes and tumor suppressor genes. One of the less well-understood aspects of oncogenesis is the change in glycosylation of certain polypeptides.

The transfer of glycosyl residues from nucleotide-activated sugar molecules to other carbohydrates or to peptides is catalyzed by glycosyltransferases, whose specificity is restricted to the formation of a single glycosidic bond linking two specific sugar residues or a sugar residue to an aglycone. The cell and tissue-specific expression of glycosyltransferases depends on the differentiation, development and malignant transformation of the cell.

Aberrant glycosylationof glycosphingolipids and glycoproteins in tumor cells has been implicated as an essential mechanism in defining stage, direction, and fate of tumor progression. Clinical studies have shown a clear correlation between aberrant glycosylation status of primary tumor and invasive/metastatic potential of human cancer as reflected by 5- or 10-year survival rates of patients. Carbohydrates expressed in tumor cells may be adhesion molecules, or may modulate adhesion receptor function. Some are known to be directly involved in cell adhesion, and are recognized by selectins or other carbohydrate-binding proteins, or by complementary carbohydrates. N- or O-glycosylation of functionally important membrane components may alter tumor cell adhesion or motility in a direction that either promotes or inhibits invasion and metastasis. Examples of such receptors are E-cadherin, integrins, immunoglobulin family receptors, e.g. CD44, and lysosome-associated membrane protein.

Alternatively, gangliosides and sphingolipids may modulate transmembrane signaling essential for tumor cell growth, invasion, and metastasis. The transducer molecules susceptible to gangliosides and sphingolipids include integrin receptors, tyrosine kinase-linked growth factor receptors, protein kinase C, and G-protein-linked receptor affecting protein kinase A. Some glycosphingolipids (e.g., Gb3Cer, Le(y), ceramide, and sphingosine induce tumor cell differentiation and subsequent apoptosis. A crucial mechanism for inhibition of metastasis may involve blocking of transmembrane signaling for expression of P- and E-selectin.

One substrate for glycosyltransferases are mucins, which are heavily glycosylated high molecular weight glycoproteins. In epithelial cancers such as colorectal cancer, both qualitative and quantitative alterations in carbohydrate and polypeptide moieties of mucin glycoproteins occur. These changes in mucin glycoproteins are one of the most common phenotypic markers of colorectal carcinogenesis and may play an important pathobiological role. The increased exposure of peptide epitopes of mucin glycoproteins in colorectal cancer appears to be due to either abnormal glycosylation or altered levels of mucin gene transcription.

Alteration of cell surface carbohydrate antigens during malignant transformation is a well-known phenomenon observed in various tumors. In prostatic carcinoma, nearly total deletion of normally occurring ABO and type I-based Lewis antigens, Le(a) and Leb, has been observed in several studies. Experimental results suggest an alteration in glycosyl transferase activity in prostatic carcinoma, with preserved or increased activity of enzymes responsible for the synthesis of the type II core sequence. During the transformation of normal cells to colon carcinoma cells, there is an increase in the presence of mucin carbohydrate moieties that are not detectable in normal cells.

The identification of proteins involved with tumor growth and metastasis is of great interest for clinical and research purposes. Understanding the involvement of glycosyl transferases, and the effect of specific changes in the glycosylation of their substrates may provide new therapeutic approaches.

RELEVANT LITERATURE

The cDNA cloning and sequencing of several human UDP-N-acetyl-alpha-D-galactosamine:polypeptide N-Acetylgalactosaminyltransferases (GALNT1, 2 and 3) have been reported, by Bennett et al. (1996) *J. Biol. Chem.* 271:17006–17012; White et al. (1995) *J. Biol. Chem.* 270:24156–24165; and Meurer et al. (1995) *J. Biochem.* 118:568–574. A general review of the molecular and cell biology of glycosyltransferases may be found in Kleene and Berger (1993) *Biochim Biophys Act.* 1154:283–325. A review of the alteration in carbohydrate moieties during malignant transformation of colon mucosa may be found in Hanski et al. (1992) Cancer Journal 5.

Loss of heterozygosity (LOH) on 3p is frequent in human renal cell carcinomas, lung cancers, and breast cancers. A detailed map of a 5 cM region on 3p24.3-25.1 flanked by D3S1286 and D3S1585, which is commonly deleted in tumors, may be found in Matsumoto et al. (1997) *Genes Chromosomes Cancer* 20:268–274. A loss of heterozygosity has also been reported in human prostatic adenocarcinoma on the 3p24-26 and 3p22-12 regions of the short arm of chromosome 3 by Dahiya et al. (1997) *Int J Cancer* 71(1):20–25. Deletion in this region have also been reported for human cutaneous squamous cell neoplasms (Sikkink et al. (1997) *J Invest Dermatol* 109(6):801–805); in squamous cell carcinoma of the head and neck (Buchhagen et al. (1996) *Head Neck* 18(6):529–537); and in transitional cell carcinoma of the urinary bladder (Li et al. (1996) *Am J Pathol* 149(1):229–235).

Public human EST sequences corresponding to ZAP-3 include AA971319; AA236602; AA055179; AA055174; AA055297; and AA368180; accessible through Genbank. A mouse EST having sequence similarity may be accessed as W12343.

SUMMARY OF THE INVENTION

Isolated nucleotide compositions and sequences are provided for ZAP-3 genes. Loss of heterozygosity at the ZAP-3 locus is associated with the oncogenesis of human cancers. The ZAP-3 nucleic acid compositions find use in identifying homologous or related genes; in producing compositions that modulate the expression or function of its encoded protein, ZAP-3; for gene therapy; mapping functional regions of the protein; and in studying associated physiological pathways.

In addition, modulation of the gene activity in vivo is used for prophylactic and therapeutic purposes, such as treatment of cancer, identification of cell type based on expression, and the like. ZAP-3, anti-ZAP-3 antibodies and ZAP-3 nucleic acid sequences are useful as diagnostics, and to identify cancers having mutations in this gene.

DESCRIPTION OF THE SPECIFIC EMBODIMENTS

ZAP-3 gene compositions and methods for their isolation are provided.

Certain human cancers, particularly epithelial cell tumors, e.g. carcinomas of the breast, colon, cervix and lung; mesotheliomas, neuroblastomas, etc., show loss of heterozygosity of ZAP-3, indicating that the gene product functions as a tumor suppressor. The ZAP-3 sequence is consistent with a predicted function as an N-acetylgalactosaminyltransferase (GALNT) involved in protein glycosylation.

The ZAP-3 genes and fragments thereof, encoded protein, and anti-ZAP-3 antibodies are useful in characterizing the phenotype of tumors that are associated with this gene. The characterization is useful for determining further treatment of the patient. Tumors may be typed or staged as to the ZAP-3 status, e.g. by detection of mutated or deleted sequences, antibody quantitation of the protein products, and functional assays for altered ZAP-3 activity levels. Tumors associated with loss of ZAP-3 include a number of carcinomas known to have deletions in the region of chromosome 3 p 24.

CHARACTERIZATION OF ZAP-3

Comparative sequence alignments indicate that ZAP-3 is a novel N-acetylgalactosaminyltransferase. The association of ZAP-3 loss of heterozygosity (LOH) with tumors and its predicted biological activity indicate that the involvement with tumorigenesis may be at the level of substrate glycosylation, possibly of cell adhesion or cell recognition molecules.

ZAP-3 forms an mRNA of approximately 4300 nt in length. It is expressed at low to moderate levels in heart, brain, placenta, lung, spleen, testes, liver, fetal brain, kidney, and skeletal muscle tissues. The chromosomal location of the human gene has been localized to 3P24. The ZAP-3 nucleic acid sequence is provided as SEQ ID NO:1, where the coding sequence extends from nt. 367 to 2284, and the encoded polypeptide sequence as SEQ ID NO:2.

At the nucleotide level there is little sequence similarity between ZAP-3 and known GalNAc transferases, however there are clear similarities at the amino acid level. A BLASTX search reveals significant similarity to both mouse and human UDP GalNAc transferases (U73819; Y08564; U70538).

IDENTIFICATION OF ZAP-3 SEQUENCES

Novel nucleic acid compositions of the invention of particular interest comprise a sequence set forth in SEQ ID NO:1 or an identifying sequence thereof. An "identifying sequence" is a contiguous sequence of residues at least about 10 nt to about 20 nt in length, usually at least about 50 nt to about 100 nt in length, that uniquely identifies a nucleic acid sequence, e.g., exhibits less than 90%, usually less than about 80% to about 85% sequence identity to any contiguous nucleotide sequence of more than about 20 nt. Thus, the subject novel nucleic acid compositions include full length cDNAs or mRNAs that encompass an identifying sequence of contiguous nucleotides from SEQ ID NO: 1.

The nucleic acids of the invention also include nucleic acids having sequence similarity or sequence identity. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate). Hybridization methods and conditions are well known in the art, see U.S. Pat. No. 5,707,829. Nucleic acids that are substantially identical to the provided nucleic acid sequences, e.g. allelic variants, genetically altered versions of the gene, etc., bind to the provided nucleic acid sequences (SEQ ID NO:1) under stringent hybridization conditions. By using probes, particularly labeled probes of DNA sequences, one can isolate homologous or related genes. The source of homologous genes can be any species, particularly grasses as previously described.

Preferably, hybridization is performed using at least 15 contiguous nucleotides of SEQ ID NO:1. The probe will preferentially hybridize with a nucleic acid or mRNA comprising the complementary sequence, allowing the identification and retrieval of the nucleic acids of the biological material that uniquely hybridize to the selected probe. Probes of more than 15 nucleotides can be used, e.g. probes of from about 18 nucleotides to not more than about 100 nucleotides, but 15 nucleotides generally represents sufficient sequence for unique identification.

The nucleic acids of the invention also include naturally occurring variants of the nucleotide sequences, e.g. degenerate variants, allelic variants, etc. Variants of the nucleic acids of the invention are identified by hybridization of putative variants with nucleotide sequences disclosed herein, preferably by hybridization under stringent conditions For example, by using appropriate wash conditions, variants of the nucleic acids of the invention can be identified where the allelic variant exhibits at most about 25–30% base pair mismatches relative to the selected nucleic acid probe. In general, allelic variants contain 5–25% base pair mismatches, and can contain as little as even 2–5%, or 1–2% base pair mismatches, as well as a single base-pair mismatch.

The invention also encompasses homologs corresponding to the nucleic acids of SEQ ID NO:1, where the source of homologous genes can be any related species within the same genus or group. Within a group, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as BLAST, described in Altschul et al., J. Mol. Biol. (1990) 215:403–10.

In general, variants of the invention have a sequence identity greater than at least about 65%, preferably at least about 75%, more preferably at least about 85%, and can be greater than at least about 90% or more as determined by the Smith-Waterman homology search algorithm as implemented in MPSRCH program (Oxford Molecular). For the purposes of this invention, a preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

The subject nucleic acids can be cDNAs or genomic DNAs, as well as fragments thereof, particularly fragments that encode a biologically active gene product and/or are useful in the methods disclosed herein. The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for expression.

The nucleic acid compositions of the subject invention can encode all or 3 part of the subject differentially expressed polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least about 15 up to about 100 contiguous nucleotides, or up to the complete sequence provided in SEQ ID NO:1. For the most part, fragments will be of at least 15 nt, usually at least 18 nt or 25 nt, and up to at least about 50 contiguous nt in length or more.

Probes specific to the nucleic acids of the invention can be generated using the nucleic acid sequences disclosed in SEQ ID NO:1 and the fragments as described above. The probes can be synthesized chemically or can be generated from longer nucleic acids using restriction enzymes. The probes can be labeled, for example, with a radioactive, biotinylated, or fluorescent tag. Preferably, probes are designed based upon an identifying sequence of a nucleic acid of one of SEQ ID NO:1. More preferably, probes are designed based on a contiguous sequence of one of the subject nucleic acids that remain unmasked following application of a masking program for masking low complexity (e.g., XBLAST) to the sequence., i.e. one would select an unmasked region, as indicated by the nucleic acids outside the poly-n stretches of the masked sequence produced by the masking program.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant", e.g., flanked by one or more nucleotides with which it is not normally associated on a naturally occurring chromosome.

The nucleic acids of the invention can be provided as a linear molecule or within a circular molecule. They can be provided within autonomously replicating molecules (vectors) or within molecules without replication sequences. They can be regulated by their own or by other regulatory sequences, as is known in the art. The nucleic acids of the invention can be introduced into suitable host cells using a variety of techniques which are available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

The subject nucleic acid compositions can be used to, for example, produce polypeptides, as probes for the detection of mRNA of the invention in biological samples (e.g., extracts of cells) to generate additional copies of the nucleic acids, to generate ribozymes or antisense oligonucleotides, and as single stranded DNA probes or as triple-strand forming oligonucleotides. The probes described herein can be used to, for example, determine the presence or absence of the nucleic acid sequences as shown in SEQ ID NO:1 or variants thereof in a sample. These and other uses are described in more detail below.

ZAP-3 NUCLEIC ACID COMPOSITIONS

Nucleic acids encoding ZAP-3 may be cDNA or genomic DNA or a fragment thereof. The term "ZAP-3 gene" shall be intended to mean the open reading frame encoding specific ZAP-3 polypeptides, introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of approximately 120 kbp; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where ZAP-3 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1:194–205; Mortlock et al (1996) *Genome Res.* 6:327–33; and Joulin and Richard-Foy (1995) *Eur J Biochem* 232:620–626.

The regulatory sequences may be used to identify cis acting sequences required for transcriptional or translational regulation of ZAP-3 expression, especially in different tissues or stages of development, and to identify cis acting sequences and trans acting factors that regulate or mediate ZAP-3 expression. Such transcription or translational control regions may be operably linked to a ZAP-3 gene in order to promote expression of wild type or altered ZAP-3 or other proteins of interest in cultured cells, or in embryonic, fetal or adult tissues, and for gene therapy.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. Such small DNA fragments are useful as primers for PCR, hybridization screening probes, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The ZAP-3 genes are isolated and obtained in substantial purity, generally as other than an intact chromosome. Usually, the DNA will be obtained substantially free of other nucleic acid sequences that do not include a ZAP-3 sequence or fragment thereof, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. Methods of probing samples for the presence of particular nucleotide sequences, as genomic DNA or RNA, are well established in the literature. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of ZAP-3 gene expression in the sample.

The sequence of a ZAP-3 gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. The ZAP-3 polypeptide is predicted to be a cytoplasmic protein localized in the endoplasmic reticulum and/or golgi apparatus.

Techniques for in vitro mutagenesis of cloned genes are known. Examples of protocols for site specific mutagenesis may be found in Gustin et al., *Biotechniques* 14:22 (1993); Barany, Gene 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp.15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, Gene Anal Tech 6:67–70 (1989); and Zhu, *Anal Biochem* 177:120–4 (1989). Such mutated genes may be used to study structure-function relationships of ZAP-3, or to alter properties of the protein that affect its function or regulation.

ZAP-3 POLYPEPTIDES

The subject gene may be employed for producing all or portions of ZAP-3 polypeptides. Fragments of interest include the glycosylation sites, which may affect the stability and/or activity of the polypeptide, the substrate binding sites for the glycosyl acceptor molecule and for the sugar-nucleotide donor molecule, the subcellular localization signals, etc. Such domains will usually include at least about 20 amino acids of the provided sequence, more usually at least about 50 amino acids, and may include 100 amino acids or more, up to the complete domain. Binding contacts may be comprised of non-contiguous sequences, which are brought into proximity by the tertiary structure of the protein. The sequence of such fragments may be modified through manipulation of the coding sequence, as described above. Truncations may be performed at the carboxy or amino terminus of the fragment, e.g. to determine the minimum sequence required for biological activity.

Assays for the biological activity of the protein or fragments thereof may be determined as described in the art. Numerous in vitro assays for determining substrate glycosylation are known in the art, (see, for examples, Smith et al. (1990) J Biol Chem 265(11):6225–6234; Fernandez-Briera et al. (1989) *Arch Int Physiol Biochim* 97(3):221–230; Koenderman et al. (1986) *Biomed Chromatogr* 1(3):104–108.) Inhibition of cellular adhesion and cell—cell contacts, as may be associated with oncogenesis, metastasis and/or angiogenesis, is determined through in vivo or in vitro models (for reviews, see Fukuda (1995) *Bioorg Med*

Chem 3(3):207–215; Zanetta et al. (1994) *Histol Histopathol* 9(2):385–412). Animal models for tumor formation are well known, and may be used to determine the effect of a polypeptide on the overall process of tumor associated morbidity and mortality.

For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a ZAP-3 gene, or may be derived from exogenous sources.

Peptides may be expressed in prokaryotes or eukaryotes in accordance with conventional ways, depending upon the purpose for expression. For large scale production, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the ZAP-3 gene in eukaryotic cells, where the ZAP-3 protein will benefit from native folding and post-translational modifications. Small peptides can also be synthesized in the laboratory. Peptides that are subsets of the complete ZAP-3 sequence may be used to identify and investigate parts of the protein important for function, or to raise antibodies directed against these regions.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the ZAP-3 gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

ANTIBODIES SPECIFIC FOR ZAP-3

The expressed ZAP-3 polypeptides are useful for the production of antibodies, where short fragments provide for antibodies specific for the particular polypeptide, and larger fragments or the entire protein allow for the production of antibodies over the surface of the polypeptide. Antibodies may be raised to the wild-type or variant forms of ZAP-3. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, New York, 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

DIAGNOSTIC USES

The subject nucleic acid and/or polypeptide compositions may be used to analyze a patient sample for deletions or mutations in ZAP-3. Biochemical studies may be performed to determine whether mutations in a ZAP-3 coding region or control regions is associated with cancers, particularly carcinomas, e.g. basal cell carcinomas, squamous carcinomas, adenocarcinomas, etc. of the skin, prostrate, breast, lung, etc.; mesothelioma, neuroblastoma, etc. Disease associated polymorphisms may include deletion or truncation of the gene, mutations that alter expression level, that affect the protein structure, etc.

A number of methods are available for analyzing nucleic acids for the presence or absence of a specific sequence. Where large amounts of DNA are available, genomic DNA is used directly. Analysis of genomic DNA may use whole chromosomes or fractionated DNA, e.g. Southern blots, etc. Comparative Genomic Hybridization (CGH), as described in U.S. Pat. No. 5,665,549, provides methods for determining the relative number of copies of a genomic sequence. The intensity of the signals from each labeled subject nucleic acid and/or the differences in the -ratios between different signals from the labeled subject nucleic acid sequencers are compared to determine the relative copy numbers of the nucleic acid sequences as a function of position along the reference chromosome spread. Other methods for fluorescence in situ hybridization are known in the art, for a review, see Fox et al. (1995) *Clin Chem* 41(11):1554–1559.

Alternatively, the region of interest is cloned into a suitable vector and grown in sufficient quantity for analysis. Cells that express ZAP-3 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990) *N.A.R.* 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine(TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. genomic DNA, amplification product or cloned fragment, is analyzed by one of a number of methods known in the art. The nucleic acid may be sequenced by dideoxy or other methods, and the sequence of bases compared to a wild-type ZAP-3 sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in ZAP-3 may be based on the functional or antigenic characteristics of the protein. Protein truncation assays are useful in detecting deletions that may affect the biological activity of the protein. Various immunoassays designed to detect polymorphisms in ZAP-3 proteins may be used in screening. Where many diverse genetic mutations lead to a particular disease phenotype, functional protein assays have proven to be effective screening tools, for example by detecting the specific glycosylation of a ZAP-3 substrate.

Changes in the promoter or enhancer sequence that may affect expression levels of ZAP-3 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Antibodies specific for a ZAP-3 may be used in staining or in immunoassays. Samples, as used herein, include cells, e.g. biopsy samples, biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal ZAP-3 in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and ZAP-3 in a lysate. Measuring the concentration of ZAP-3 binding in a sample or fraction thereof may be accomplished by a variety of specific assays. A conventional sandwich type assay may be used. For example, a sandwich assay may first attach ZAP-3-specific antibodies to an insoluble surface or support. Patient sample lysates are then added to the supports (for example, separate wells of a microtiter plate) containing antibodies. Preferably, a series of standards, containing known concentrations of normal and/or abnormal ZAP-3 is assayed in parallel with the samples or aliquots thereof to serve as controls. The quantitation may then be performed by adding a labeled antibody specific for ZAP-3. Other immunoassays are known in the art and may find use as diagnostics. Ouchterlony plates provide a simple determination of antibody binding. Western blots may be performed on protein gels or protein spots on filters, using a detection system specific for ZAP-3 as desired, conveniently using a labeling method as described for the sandwich assay.

MODULATION OF GENE EXPRESSION

The ZAP-3 genes, gene fragments, or the encoded protein or protein fragments are useful in gene therapy to treat disorders associated with ZAP-3 defects. Expression vectors may be used to introduce the ZAP-3 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus;, e.g. lentivirus; adenovirus; and the like, where the vectors are able to transiently or stably be maintained in the cells, usually for a period of at least about one day, more usually for a period of at least about several days to several weeks.

The gene or ZAP-3 protein may be introduced into tissues or host cells by any number of routes, including viral infection, microinjection, or fusion of vesicles. Jet injection may also be used for intramuscular administration, as described by Furth et al. (1992) *Anal Biochem* 205:365–368. The DNA may be coated onto gold microparticles, and delivered intradermally by a particle bombardment device, or "gene gun" as described in the literature (see, for example, Tang et al. (1992) *Nature* 356:152–154), where gold microprojectiles are coated with the ZAP-3 or DNA, then bombarded into skin cells.

Antisense molecules can be used to down-regulate expression of ZAP-3 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

GENETICALLY ALTERED CELL OR ANIMAL MODELS FOR ZAP-3 FUNCTION

The subject nucleic acids can be used to generate transgenic animals or site specific gene modifications in cell lines. Transgenic animals may be made through homologous recombination, where the normal ZAP-3 locus is altered. Alternatively, a nucleic acid construct is randomly integrated into the genome. Vectors for stable integration include plasmids, retroviruses and other animal viruses, YACs, and the like.

The modified cells or animals are useful in the study of ZAP-3 function and regulation. For example, a series of small deletions and/or substitutions may be made in the ZAP-3 gene to determine the role of different exons in oncogenesis, protein-protein interactions, etc. Of interest are the use of ZAP-3 to construct transgenic animal models for cancer or metastasis, where expression of ZAP-3 is specifically reduced or absent, e.g. in epithelial tissue, etc. Conditional knock-outs are of interest, where the gene is inactivated only after exposure to a defined signal, for example by introduction of lox sites flanking the ZAP-3 gene, in combination with an inducible Cre expression construct. Specific constructs of interest include antisense ZAP-3, which will block ZAP-3 expression, expression of dominant negative ZAP-3 mutations, and conditional expression of ZAP-3 genes.

DNA constructs for homologous recombination will comprise at least a portion of the ZAP-3 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on oncogenesis, metastasis, etc.

IN VITRO MODELS FOR ZAP-3 FUNCTION

Drug screening may be performed using a genetically altered cell or animal, purified ZAP-3 protein, or ZAP-3 protein in combination with other cellular proteins. Of particular interest is the identification of the ZAP-3 substrate for glycosylation, and the structure of the resulting carbohydrate moiety. The ZAP-3 product may then be analyzed for its role in cell adhesion, signaling, etc. One can identify ligands or substrates that bind to, modulate or mimic the action of ZAP-3. Areas of investigation include the development of cancer treatments, metastasis, etc.

Drug screening identifies agents that provide a replacement for ZAP-3 function, that modulate ZAP-3 expression, or may be directed to the ZAP-3 carbohydrate product, i.e. compounds that mimic the biological activity of the carbohydrate, or that interfere with the binding of the carbohydrate to its receptor. ZAP-3 carbohydrate product is also of interest for modeling extracellular adhesion and contacts that may be compromised during metastasis. Analogs of these compounds may be developed based on ZAP-3 protein activity on a substrate.

Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, etc.

The term "agent" as used herein describes any molecule, e.g. protein or pharmaceutical, with the capability of altering or mimicking the physiological function of ZAP-3. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding.

Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of cancer, etc. The therapeutic agents may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The following examples are offered by illustration not by way of limitation.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Characterization of ZAP-3

Materials and Methods

LOH analysis. Primer sequences flanking polymorphic microsatellite loci were obtained from the Whitehead Genome Center Database (http://www-genome.wi.mit.edu/cgi-bin/contig/phys_map). PCR amplification, PCR product analysis, and calculation of the allelic ratios of heterozygous loci was performed essentially as described (Larson et al. (1997) *Cancer Research* 57:4082–4090). Tumor specimens and cell lines. Tumor specimens and matched non-involved tissue were provided by Memorial Sloan-Kettering Cancer Center. Cell Lines were provided by Memorial Sloan-Kettering Cancer Center and University of Tokyo. DNAs were extracted as previously described (Hampton et al. (1994) *PNAS* 91:6953–6957).

cDNA selection. cDNA selection was performed as previously described (Lovett et al. (1991) *PNAS* 88:9628–9632, Morgan et al. (1992) *Nuc. Acids Res.* 20:5173–5179) and cDNA selection products were cloned into pCR2.1 as directed by the manufacturer (Invitrogen, Carlsbad, Calif.).

cDNA libraries. Fetal brain (Clontech, Palo Alto, Calif.) and adult frontal cortex (Stratagene, La Jolla, Calif.) cDNA libraries were screened as directed by the manufacturer.

Northern analysis. Human adult and fetal multiple tissue Northern blots were purchased from Clontech (Palo Alto, Calif.).

BAC sequencing. DNA from BAC clones was prepared using Qiagen DNA prep kits and further purified by CsCl gradient. DNA was sonicated and DNA fragments were repaired using nuclease BAL-31 and T4 DNA polymerase. DNA fragments of 0.8–2.2 kb were size-fractionated by agarose gel electrophoresis and ligated into pUC9 vector. Inserts of the plasmid clones were amplified by PCR and sequenced using standard ABI dye-primer chemistry (ABI, Foster City, Calif.). Preliminary sequence analysis and assembly were performed using the InnerPeace(IP) system developed at Sequana Theraputics Inc. (La Jolla, Calif.

The ZAP-3 gene spans 55 kb of the human genome on chromosome 3p24. The gene and protein sequences are provided as SEQ ID NO:1. There are ten exons, as follows:

| Genomic Structure of ZAP-3 | | | |
|---|---|---|---|
| exon | size (bp) | intron | size (bp) |
| 1 | 538 | 1 | 20065 |
| 2 | 166 | 2 | 4693 |
| 3 | 204 | 3 | 7644 |
| 4 | 167 | 4 | 2454 |
| 5 | 117 | 5 | 1328 |
| 6 | 194 | 6 | 6532 |
| 7 | 131 | 7 | 376 |
| 8 | 104 | 8 | 2602 |
| 9 | 143 | 9 | 4595 |
| 10 | 146 | | |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated cDNA molecule that will hybridize under stringent conditions of 50° C. or higher in the presence of 0.1×SSC to the sequence set forth in SEQ ID NO;1, wherein said cDNA encodes a mammalian N-acetylgalactosaminyltransferase ZAP-3 protein.

2. An isolated cDNA molecule, wherein said cDNA encodes the amino acid sequence set forth in SEQ ID NO:2.

3. An isolated cDNA molecule, wherein said cDNA comprises the nucleotide sequence of SEQ ID NO:1.

4. A cell comprising a recombinant nucleic acid comprising a ZAP-3 cDNA sequence that will hybridize under stringent conditions of 50° C. or higher in the presence 0.1×SSC to the sequence set forth in SEQ ID NO:1, wherein said cDNA encodes a mammalian N-acetylgalactosaminyltransferase ZAP-3 protein..

5. An isolated nucleic acid molecule consisting of a sequence of at least 50 contiguous nucleotides of the sequence set forth in SEQ ID NO:1.

6. An isolated nucleic acid molecule consisting of a sequence of at least 100 contiguous nucleotides of the sequence set forth in SEQ ID NO: 1.

7. A vector comprising a ZAP-3 cDNA sequence that hybridizes under stringent conditions, at 50° C. or higher in the presence of 0.1×SSC, to the sequence set forth in SEQ ID NO:1 wherein said cDNA encodes a mammalian N-acetylgalactosaminyltransferase ZAP-3 protein.

8. The isolated cDNA of claim 7, wherein said vector comprises a expression cassette comprising a transcription initiation region operably linked to said ZAP-3 cDNA sequence.

9. The isolated cDNA of claim 7, wherein said vector is a plasmid.

10. The isolated cDNA of claim 7, wherein said vector is a retrovirus.

11. The isolated cDNA of claim 7, wherein said vector is an adenovirus.

12. The cell according to claim 4, wherein said ZAP-3 cDNA sequence is operably linked to a expression cassette comprising a transcription initiation region.

* * * * *